US008208711B2

(12) United States Patent
Venkatachalam et al.

(10) Patent No.: US 8,208,711 B2
(45) Date of Patent: Jun. 26, 2012

(54) METHOD FOR AUTOMATIC IDENTIFICATION OF DEFECTS IN TURBINE ENGINE BLADES

(75) Inventors: Rajashekar Venkatachalam, Banagalore (IN); Mahesh Kumar Asati, Bangalore (IN); Prakash Mandayam Comare, Chennai (IN); Megha Navalgund, Bangalore (IN); Xiaoming Liu, Schenectady, NY (US); Robert August Kaucic, Niskayuna, NY (US); Joseph Manuel Portaz, Hamilton, OH (US); Manoharan Venugopal, Bangalore (IN)

(73) Assignee: General Electric Company, Niskayuna, NY (US)

( * ) Notice: Subject to any disclaimer, the term of this patent is extended or adjusted under 35 U.S.C. 154(b) by 1049 days.

(21) Appl. No.: 11/851,422

(22) Filed: Sep. 7, 2007

(65) Prior Publication Data

US 2009/0066939 A1    Mar. 12, 2009

(51) Int. Cl.
*G06K 9/00* (2006.01)
*G01N 23/00* (2006.01)
*G21K 7/00* (2006.01)

(52) U.S. Cl. .......... 382/141; 348/86; 348/125; 250/306; 356/237.1

(58) Field of Classification Search ................. 382/141, 382/142–152; 250/306–311; 348/86–95, 348/125–134; 700/95–212; 29/833; 438/16; 356/237.1–237.6, 426–431; 702/35–40
See application file for complete search history.

(56) References Cited

U.S. PATENT DOCUMENTS

| 4,803,639 | A | * | 2/1989 | Steele et al. | 702/40 |
|---|---|---|---|---|---|
| 4,809,314 | A | * | 2/1989 | Steele et al. | 378/205 |
| 5,111,046 | A | * | 5/1992 | Bantel | 250/330 |
| 5,764,721 | A | * | 6/1998 | Light et al. | 378/4 |
| 6,701,615 | B2 | * | 3/2004 | Harding et al. | 29/889.1 |
| 6,894,303 | B2 | * | 5/2005 | Livingston | 250/585 |
| 7,334,993 | B2 | * | 2/2008 | Sekihara et al. | 416/97 R |
| 2003/0099330 | A1 | * | 5/2003 | Mery et al. | 378/210 |
| 2003/0132395 | A1 | * | 7/2003 | Livingston | 250/458.1 |
| 2003/0167616 | A1 | * | 9/2003 | Harding et al. | 29/407.05 |
| 2004/0021101 | A1 | * | 2/2004 | Livingston | 250/588 |
| 2004/0066538 | A1 | * | 4/2004 | Rozzi | 358/2.1 |
| 2007/0065283 | A1 | * | 3/2007 | Sekihara et al. | 416/97 R |
| 2009/0066939 | A1 | * | 3/2009 | Venkatachalam et al. | 356/237.1 |
| 2009/0097729 | A1 | * | 4/2009 | Venkatachalam et al. | 382/132 |

FOREIGN PATENT DOCUMENTS

EP          48568      *   3/1982

OTHER PUBLICATIONS

Research Automatic Inspection Techniques of Real-Time Radiography for Turbine-Blade Jixie Gongcheng Xuebao (Chinese Journal of Mechanical Engineering) (China) vol. 41, No. 4, pp. 180-184 Apr. 2005.

* cited by examiner

*Primary Examiner* — Aaron W Carter
(74) *Attorney, Agent, or Firm* — Richard DeCristofaro

(57) ABSTRACT

A method for automatically identifying defects in turbine engine blades is provided. The method comprises acquiring one or more radiographic images corresponding to one or more turbine engine blades and identifying one or more regions of interest from the one or more radiographic images. The method then comprises extracting one or more geometric features based on the one or more regions of interest and analyzing the one or more geometric features to identify one or more defects in the turbine engine blades.

20 Claims, 6 Drawing Sheets

METHOD FOR AUTOMATIC IDENTIFICATION OF DEFECTS IN TURBINE ENGINE BLADES

BACKGROUND

The invention relates generally to turbine engines and more specifically to a method for automatically identifying and classifying defects in turbine engine blades.

Turbine engines essentially consist of an air compressor, a combustion chamber and a turbine. The compressors compress air which is mixed with fuel and channeled to the combustor. The compressed air mixed with fuel is ignited within the combustion chamber to generate combustion gases, which are then channeled to the turbine. Within the turbine, the hot combustion gases blow over the turbine blades. Cooling channels in the turbine engine blades receive cooler air from the compressor of the turbine engine and pass air through the blades. Holes in the leading and trailing edges of the blades form showerheads for exhausting cooling fluids from the internal passages to provide film cooling on the outer surfaces of the turbine blades. As will be appreciated by those skilled in the art, the size, shape and angle of the cooling holes determine the effectiveness of the cooling flow and can have an impact on the airflow pattern over the surface of the blades. However, during manufacturing, certain defects (for example, caused by poor laser drilling techniques or by the presence of residual core material) may be formed in these holes, leading to the formation of blocked cooling holes, leading to excessive or uneven heating and ultimately damaged turbine blades.

These defects may generally be identified through manual inspections of the X-ray images of the turbine blade after the application of image processing enhancement algorithms. Automated defect recognition techniques may also be used to identify defects in turbine blades. However, these techniques are typically based on statistical analysis and require huge reference databases to perform defect classification and identification. Moreover, these approaches involve significant training effort and set up time.

It would be desirable to develop an efficient technique for automatically identifying defects in turbine engine blades that improves throughput, reduces inspection cost and improves inspection quality.

BRIEF DESCRIPTION

Embodiments of the present invention address this and other needs. In one embodiment, a method for automatically identifying defects in turbine engine blades is provided. The method comprises acquiring one or more radiographic images corresponding to one or more turbine engine blades and identifying one or more regions of interest from the one or more radiographic images. The method then comprises extracting one or more geometric features based on the one or more regions of interest and analyzing the one or more geometric features to identify one or more defects in the turbine engine blades.

In another embodiment, a system for automatically identifying defects in turbine engine blades is provided. The system includes a feature segmentation component, a feature identification component and a defect identification component. The feature segmentation component is configured to identify one or more regions of interest in one or more radiographic images corresponding to one or more turbine engine blades. The feature identification component is configured to extract one or more geometric features based on the regions of interest and the defect identification component is configured to analyze the geometric features to identify one or more defects in the turbine engine blades.

DRAWINGS

These and other features, aspects, and advantages of the present invention will become better understood when the following detailed description is read with reference to the accompanying drawings in which like characters represent like parts throughout the drawings, wherein:

FIG. 3(*b*) is an illustration of an edge image generated for a turbine engine blade, identifying the left boundary of a coolant channel in the turbine engine blade;

DETAILED DESCRIPTION

Figure 1:
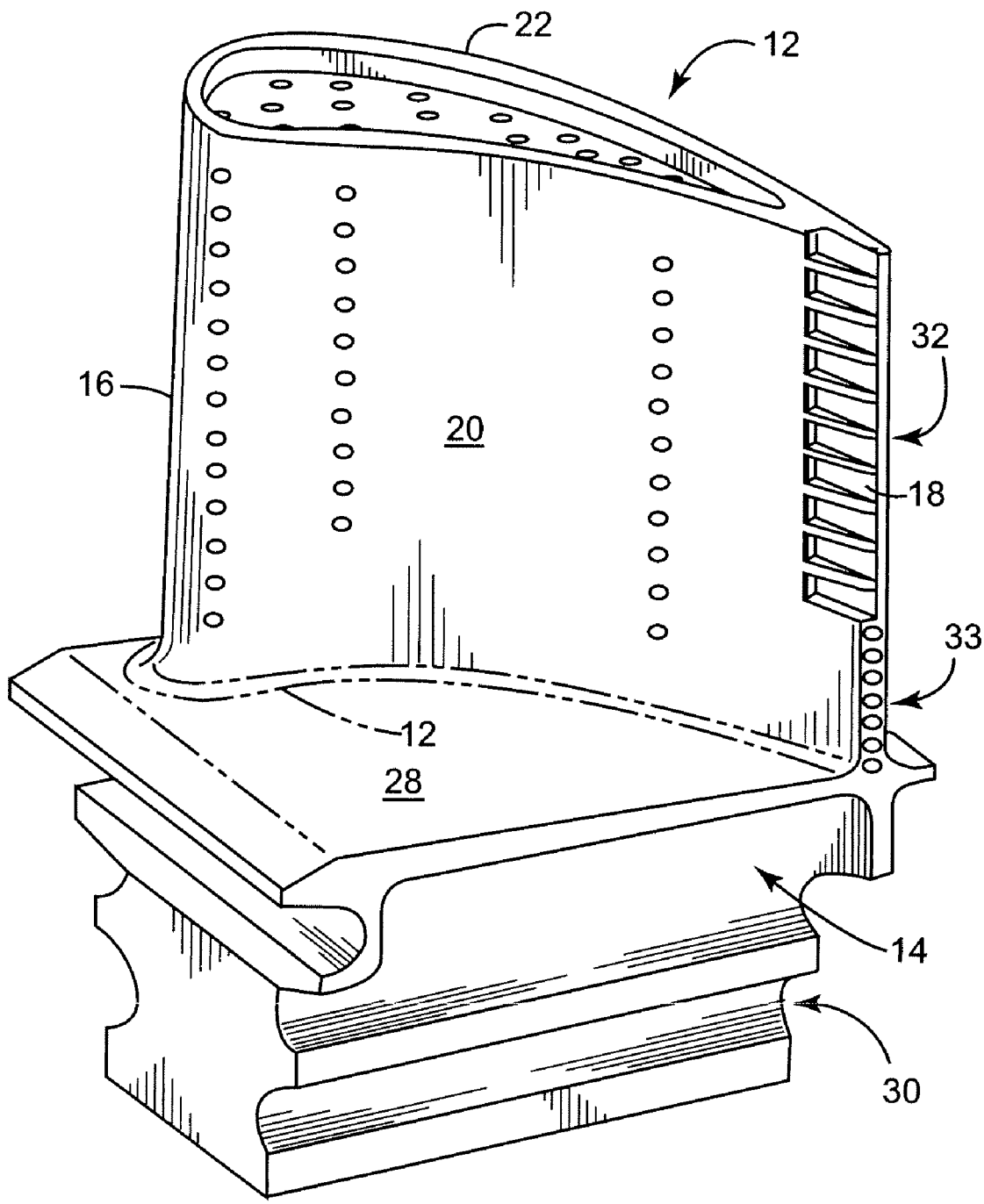
FIG. 1 is a perspective view of an exemplary turbine engine blade.

FIG. 1 is a perspective view of an exemplary turbine engine blade. As shown in FIG. 1, a turbine engine blade generally includes an airfoil 12 connected to a shank 14. The airfoil 12 is composed of a leading edge 16, a trailing edge 18, a pressure side wall 20 and a suction side wall 22. The pressure side wall 20 is connected to the suction side wall 22 at the leading edge 16 and the trailing edge 18. The airfoil 12 further includes a tip 24 and a root 26 connected by the pressure side wall 20, the suction side wall 22, the leading edge 16 and the trailing edge 18. The shank 14 includes a platform 28 and a dovetail 30. The airfoil 12 is connected at the root 26 to the platform 28. The turbine engine blade further includes at least one cooling cavity within the body of the turbine blade. The cooling cavity is in flow communication with a plurality of trailing edge holes or cooling holes 32 which extend along the trailing edge 18 and a plurality of trailing edge openings 33, extending through the trailing edge 18. Cooling gases flow through the turbine blade and are expelled from the blade through the plurality of trailing edge holes 32 in the trailing edge 18. The cooling cavity is typically formed from a plurality of cooling channels. In general, the cooling channels receive air from the compressor (not shown in FIG. 1) of the turbine engine and pass the air through the turbine blade and out through the trailing edge holes 32. This cooling air flows over the surface of the turbine engine blade to cool the upper and lower portions of the trailing edge 18.

Figure 2:
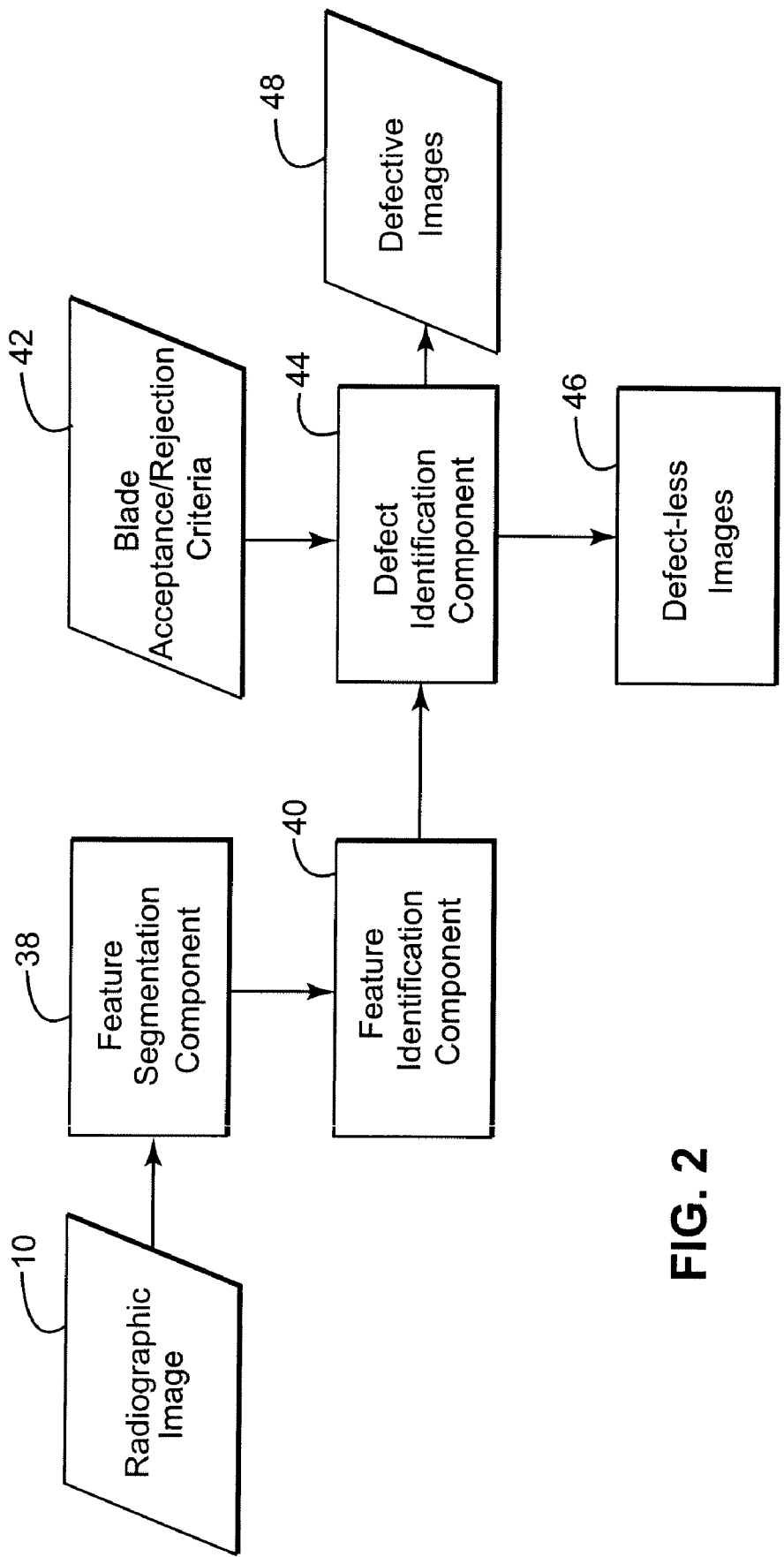
FIG. 2 is a high level illustration of a process for automatically identifying defects in a turbine engine blade, in accordance with one embodiment of the invention.

FIG. 2 is a high level illustration of a system for automatically identifying defects in a turbine engine blade, in accordance with one embodiment of the invention. In accordance with embodiments of the present invention, the turbine engine blade is inspected automatically using its radiographic image. In a particular embodiment, and as will be described in greater detail below, the radiographic image is automatically analyzed to identify and classify one or more defects in the turbine engine blade, based on a plurality of features extracted from the radiographic image of the turbine engine blade. The plurality of features may be extracted and analyzed using one or more image processing techniques such as, for example, laplacian edge detection, connected components, second derivative profiles and anisotropic diffusion.

Figure 3B:
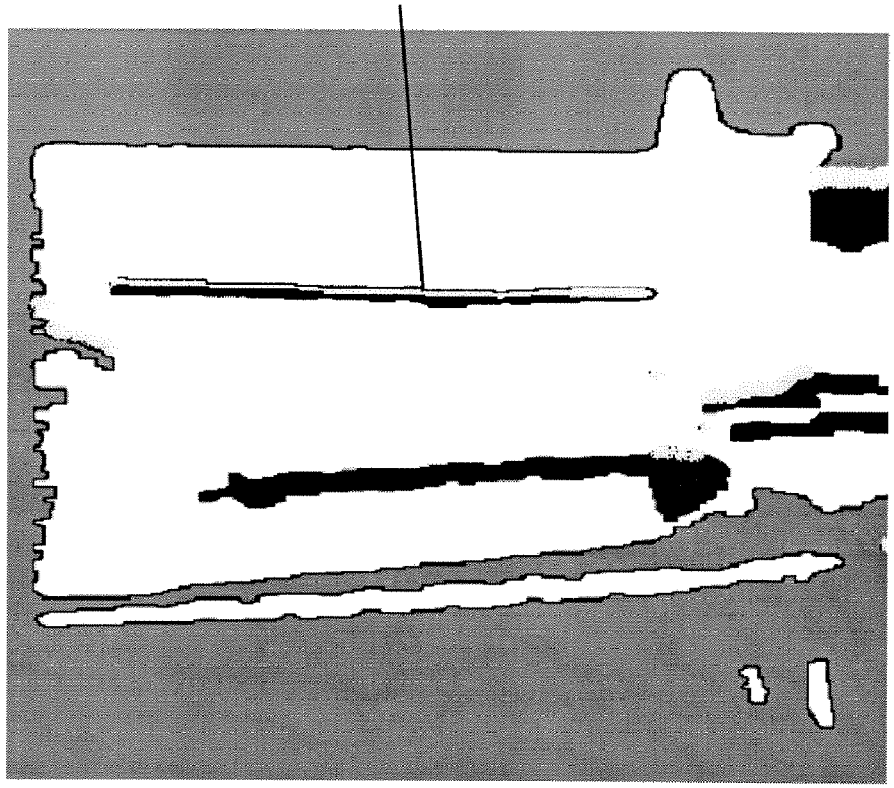
FIG. 3(*a*) is an illustration of an edge image generated for a turbine engine blade, identifying the right boundary of a coolant channel in the turbine engine blade.
Figure 3A:
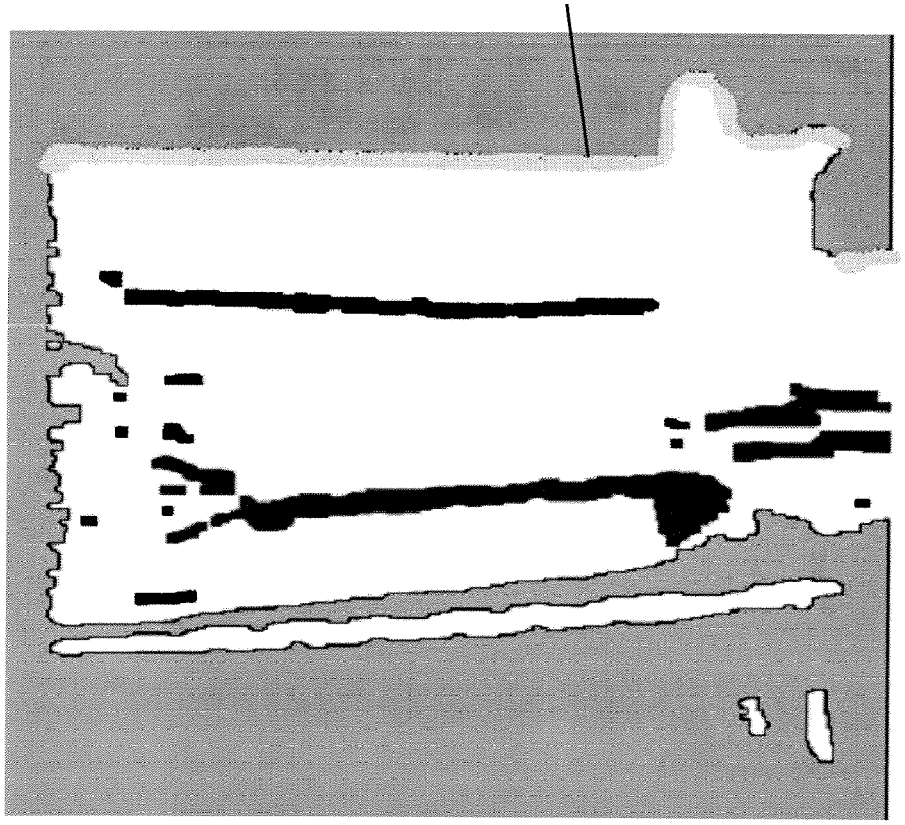

Referring to FIG. 2, a radiographic image 10 of a turbine engine blade to be inspected is acquired. In one embodiment, the radiographic image 10 may be acquired using an X-ray system comprising an X-ray source and a linear detector. A feature segmentation component 38 is configured to identify one or more regions of interest in the radiographic image 10 of the turbine engine blade. In one embodiment, the feature segmentation component 38 is configured to generate an edge image corresponding to one or more cooling channels in the turbine engine blade from the radiographic image 10. In a particular embodiment, the edge image is generated using a laplacian edge detection technique. As will be appreciated by those skilled in the art, a laplacian edge detection technique uses a linear function to represent required edge information in an image. In particular, the laplacian edge detection technique uses a two-dimensional linear filter to approximate a second order derivative of pixel values of the image to detect edges in an image. An anisotrophic diffusion technique may further be applied to suppress edge features that get highlighted due to inherent noise present in the radiographic image 10. As will be appreciated by those skilled in the art, an anisotropic diffusion technique uses diffusion filters to improve an image qualitatively by removing noise and preserving image details and enhancing image edges. FIG. 3(a) is an illustration of an edge image generated for a turbine engine blade, identifying the right boundary of a coolant channel in the turbine engine blade. FIG. 3(b) is an illustration of an edge image generated for a turbine engine blade, identifying the left boundary of a coolant channel in the turbine engine blade. As may be observed from FIG. 3(a) and FIG. 3(b), the identification of the right and the left boundaries from the edge detected images enables the accurate detection of the alignment of the holes along the trailing edge of the turbine engine blade. In particular, the right boundary 50 shown in FIG. 3(a) defines the end points of the alignment of the holes along the trailing edge and the left boundary 52 shown in FIG. 3(b) defines a vertical channel that the holes in the trailing edge connect to.

Figure 4:
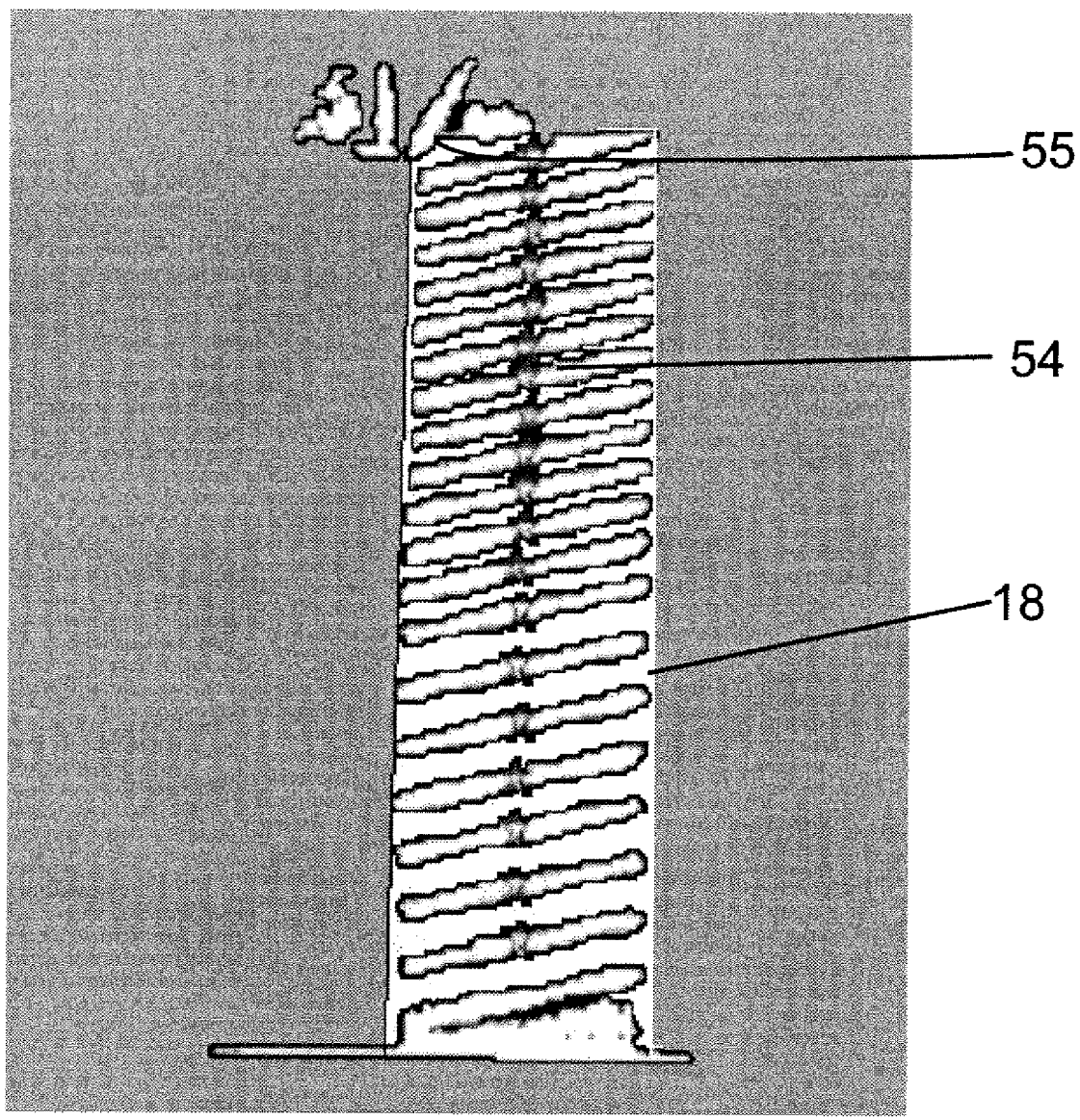
FIG. 4 is an illustration of an exemplary processed radiographic image of the trailing edge region in a turbine engine blade.

The feature segmentation component 38 may further be configured to extract a region of interest corresponding to the trailing edge 18 of the turbine engine blade, automatically from the edge detected images, shown in FIG. 3(a) and FIG. 3(b) respectively. FIG. 4 is an illustration of a radiographic image of the trailing edge region in a turbine engine blade. In one embodiment, the region of interest 54 corresponding to the trailing edge is extracted by initially traversing from the rightmost column (right boundary of the vertical trailing edge) of the radiographic image inwards until a vertical edge is met. The process of traversing is then repeated further inwards into the radiographic image to extract the left boundary of the trailing edge.

Referring to FIG. 2 again, a feature identification component 40 is configured to extract one or more geometric features, based on the regions of interest identified by the feature segmentation component 38. In one embodiment, the feature identification component 14 is configured to segment one or more trailing edge holes 32 in the region of interest, along the trailing edge 18 of the turbine blade. In a particular embodiment, a plurality of techniques based on connected components (to perform robust outlier rejection), centroid computation (to accurately fit lines to model the trailing edge holes) and outlier identification may be used to segment the trailing edge holes 32. In one embodiment, the region of interest comprising the left and right boundaries of the trailing edge region as described in FIG. 4 above, is used to extract the trailing edge holes. As will be appreciated by those skilled in the art, the radiographic image (i.e., the Laplacian of Gaussian image corresponding to the region of interest) includes trailing edge holes and other un-desired regions. In a particular embodiment, connected components are used to determine the different connected regions in the radiographic image. In addition, parameters for each connected component region such as, for example, area, centroid and minor axis length are determined. These parameters may be used to identify the regions corresponding to the trailing edge holes and remove other un-desired regions in the image. The required number of trailing edge holes to be identified is then determined. If the number of trailing edge holes identified is greater than the specification of the turbine engine blade, the connected regions at the bottom portion of the trailing edge region, (i.e., from the base of the turbine blade) are removed. If the number of trailing edge holes identified is less than the number of holes that are required to be present as per the specification of the turbine engine blade, then the turbine blade is classified as defective with the defect type being classified as a missing hole. In another embodiment, the trailing edge holes may also be extracted based on the geometric characteristics of the turbine engine blade. In a particular embodiment, a region of interest at the intersection of the $20^{th}$ hole 55 with the left boundary is used to segment the trailing edge holes that intersect the bulb of the turbine engine blade as shown in FIG. 4.

The extracted geometric features from the feature segmentation component 38 and the feature identification component 40 may then be further analyzed by a defect identification component 44 to identify one or more defects in the turbine engine blades. In one embodiment, the defects represent geometrical defects (such as, based on the width, depth or contrast in the turbine engine blade) that occur at certain regions in the turbine engine blade. In a particular embodiment, the defects may include, but are not limited to, missing holes, dwells, overdrills, merges, misdrills and scarfs.

Figure 5:
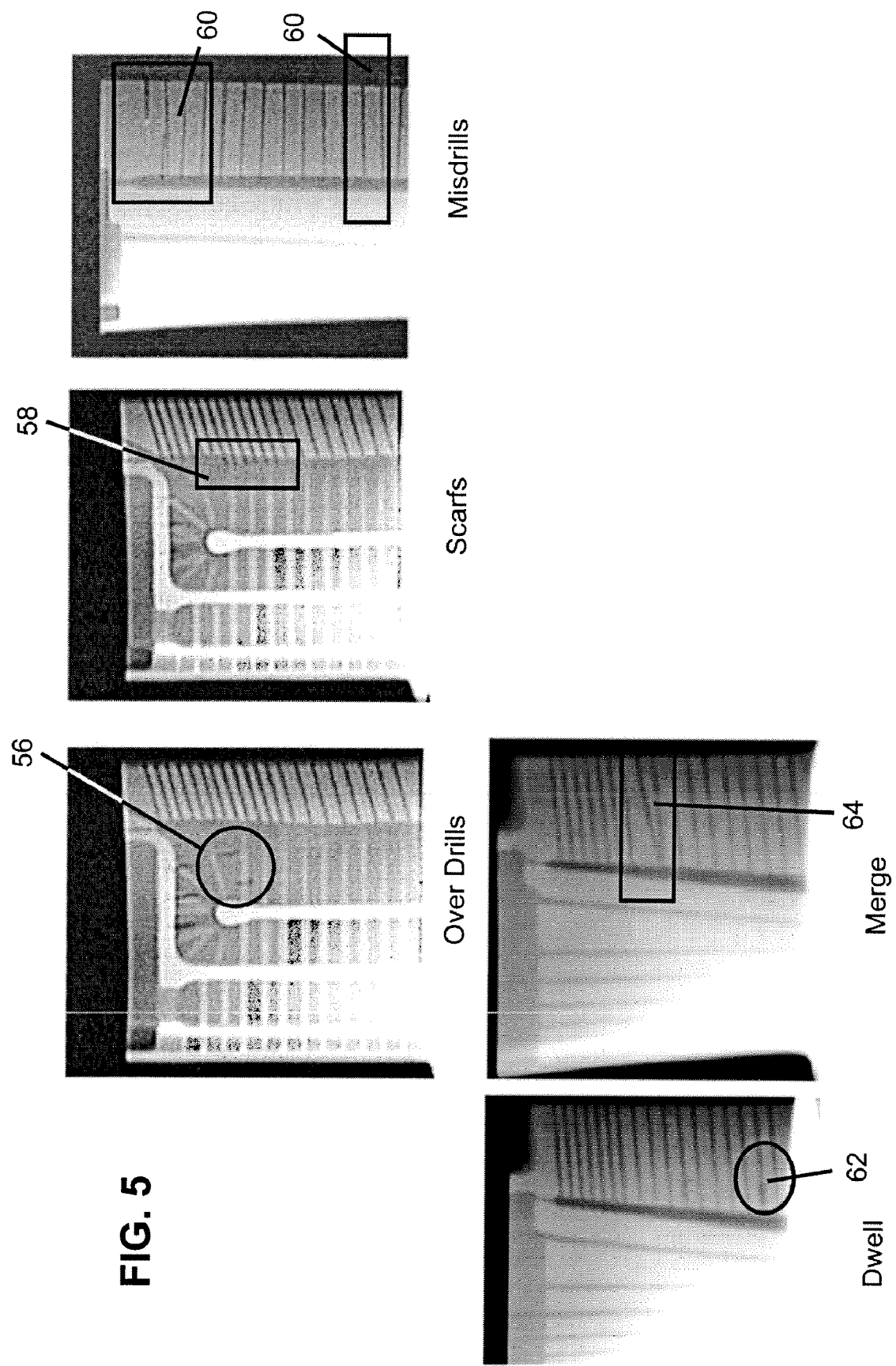
FIG. 5 illustrates a plurality of radiographic images identifying one or more defects in a turbine engine blade.

FIG. 5 illustrates a plurality of radiographic images identifying one or more defects in a turbine engine blade. As shown in FIG. 5, the defects may generally be classified as overdrills 56, scarfs 58, misdrills 60, dwells 62 and merges 64.

In one embodiment, dwells 62 are identified based on the thickness deviation of each drilled trailing edge hole identified by the feature identification component 40. In one embodiment, relative contrast measures are used to identify the regions of interest in the radiographic image that represent dwells 62. As used herein, the "relative contrast measure" is defined as the ratio of the intensity/gray level value difference of two adjacent image areas representing different material thickness and the means of these intensities (determined by the background image values). In a particular embodiment, thickness variations in the pixels for each hole along the vertical direction are directly determined from the width of the segmented trailing edge holes and the thickness variations in the pixels for each hole along the horizontal direction are determined based on the differences in the intensity values/gray level values within the hole. In general, an increase in the thickness variation along the horizontal direction, results in a difference in the contrast measure (i.e., the region of interest appears darker than the other regions comprising the same hole or neighboring holes that do not contain a dwell).

Merges 64 are identified based on the intersection of the drilled trailing edge holes identified by the feature identification component 40. In one embodiment, merges 64 may be identified based on the distance in pixels between two adjacent trailing edge holes. In a particular embodiment, merges 64 may be identified if the distance in pixels between two trailing edge holes at a few consecutive points is away from the median distance between them and if the trailing edge holes intersect each other.

Overdrills 56 may be identified based on the extrapolation of the drilled trailing edge holes beyond a particular drilled hole. In one embodiment overdrills 56 may be also identified based on a change in the contrast value inside the bulb cavity region of the turbine engine blade.

Misdrills 60 may be identified based on the intersection of one or more top holes with the radial hole in the turbine engine blade. In one embodiment, misdrills 60 may further be identified when the top hole intersects with the smaller diameter of the radial hole instead of the larger diameter or transition region.

As will be appreciated by those skilled in the art, scarfs 58 may be created because of excess removal of material due to drilling at certain locations. Scarfs generally appear as dark patches in the image and are usually identified based on relative contrast values. In one embodiment, relative contrast measures are used to identify the regions of interest in the radiographic image that represent scarfs 58. In one embodiment, scarfs 58 may be produced as a result of drilling a refresher hole along the trailing edge region and may be created when the refresher hole breaks into the turnaround cavity of the turbine engine blade.

In accordance with embodiments of the present invention, at least one of a turbine engine blade acceptance criterion 42 and/or a turbine engine blade rejection criterion 42 may be characterized according to turbine blade design and further be applied to one or more of the extracted features to identify one or more of the defects in the turbine blade. In a particular embodiment, a defect classification for each turbine blade is performed by the defect identification component 44, based on the extracted features and the acceptance/rejection criteria 42 to identify the defects in the turbine blade. In one example, the acceptance/rejection criteria 42 for detecting dwells 62 may be based on determining the number of dwells that are permitted in any given trailing edge hole and dwells that are present in adjacent cooling holes. The criteria 42 may also be based on certain geometrical features present in the trailing edge hole, such as, for example, the minimum spacing between the trailing edge holes and the size (diameter and length) of the dwell in between the trailing edge holes. In another example, the acceptance/rejection criteria 42 for detecting merges 64 in trailing edge holes may be based on the maximum number of merges that can occur in the trailing edge holes (for example, two holes per merge with a 0.005" maximum overlap).

Referring to FIG. 2 again, the radiographic images 10 are then automatically classified as either defective images 48 or defect-less images 46 based on the extracted geometric features and the turbine engine blade acceptance and rejection criteria. In one embodiment, the approximate location of the defective image 48 may also be determined and screened by an operator for further analysis. Therefore, in accordance with embodiments of the present invention, only the defective images that need operator intervention are further analyzed, thereby increasing throughput, reducing inspection cost, and improving the quality of inspection.

Figure 6:
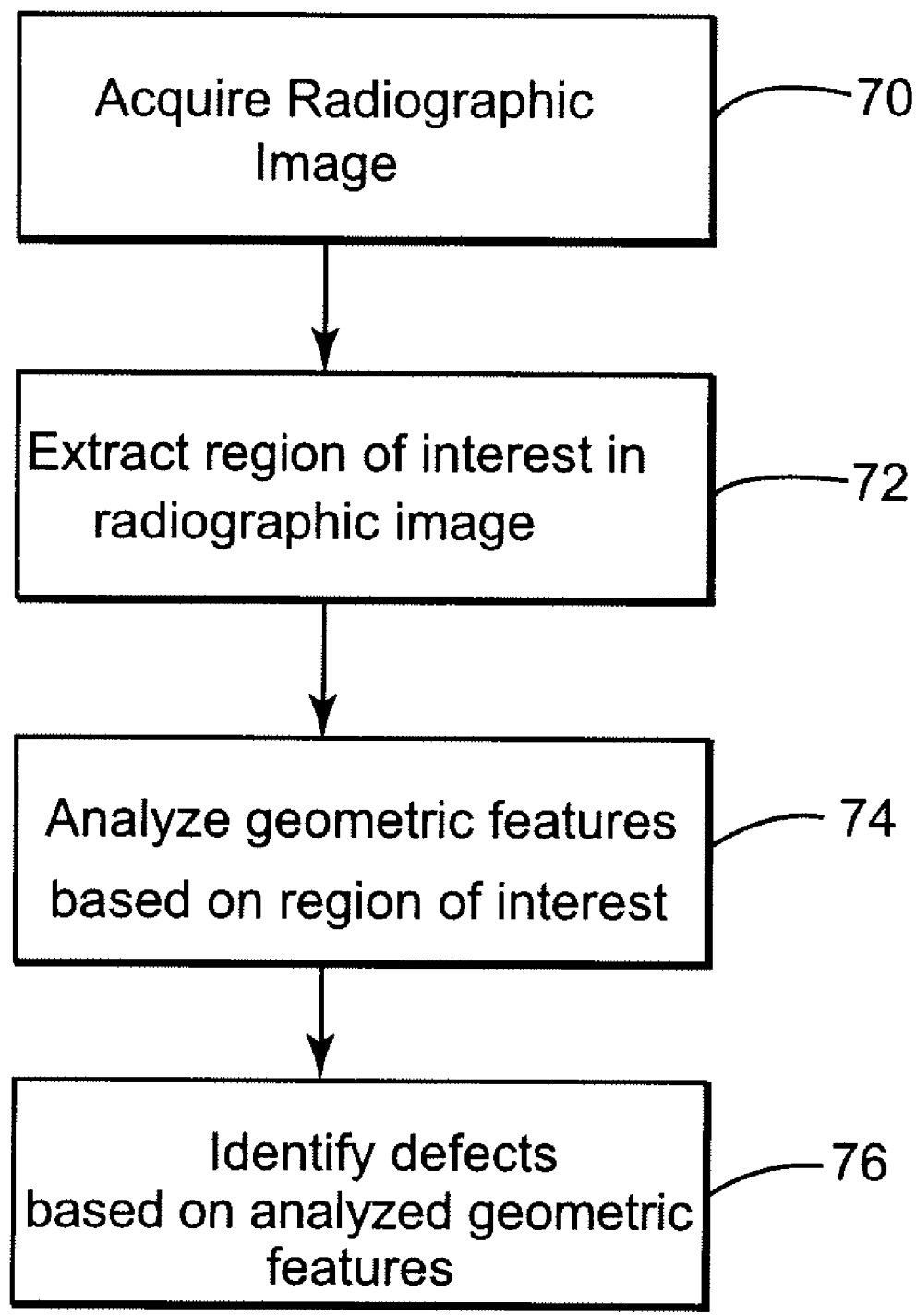
FIG. 6 is a flowchart illustrating exemplary process steps for automatically identifying defects in turbine engine blades, in accordance with one embodiment of the invention.

FIG. 6 is a flowchart illustrating exemplary process steps for automatically identifying defects in turbine engine blades, in accordance with one embodiment of the invention. In step 70, one or more radiographic images 10 of a turbine blade are acquired using an X-ray system. In step 72, one or more regions of interest are identified from the radiographic image 10. As mentioned above, identifying one or more regions of interest comprises generating an edge image corresponding to one or more cooling channels in the turbine engine blades, from the radiographic image. In step 74, one or more geometric features are extracted based on the regions of interest. As mentioned above, extracting the geometric features based on the regions of interest comprises segmenting one or more trailing edge holes along the trailing edge region of the turbine blade. In step 76, the geometric features are analyzed to identify one or more defects in the turbine engine blade. In one embodiment, a turbine engine blade acceptance criteria and/or a turbine engine blade rejection criteria are applied to the turbine engine blade, based on the extracted geometric features, to identify the defects in the turbine engine blade. The defects may include, but are not limited to, dwells, overdrills, merges, misdrills and scarfs. As mentioned above, dwells may be identified either based on the thickness variation in the number of pixels for each hole along the vertical direction or based on gray value changes within the hole. Scarfs may be identified based on the relative contrast measures obtained in regions of occurrence of scarfs. Overdrills may be identified by extrapolating the trailing edge holes beyond a boundary. Merges may be identified based on an intersection of adjacent holes or based on distances between two successive holes. Misdrills may be identified based on a region of intersection of one or more top holes with the radial hole The disclosed embodiments have several advantages including the ability to automatically extract a region of interest corresponding to one or more geometric features, from a radiographic image of a turbine engine blade. The technique for identifying and classifying defects in turbine engine blades disclosed in accordance with embodiments of the present invention is not dependent on statistical parameters or reference images. Further, the disclosed technique takes into account positioning shifts in the placement of the turbine blades and is robust to slight shifts in the positioning of the turbine engine blade. In addition, in accordance with embodiments of the present invention, only the defective images that need operator intervention are further analyzed, thereby increasing throughput, reducing inspection cost, and improving the quality of inspection. Therefore, the reliability of turbine blade inspection is improved by reducing the operator's subjectivity while performing manual inspections.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for automatically identifying geometric defects in turbine engine blades, comprising the steps of:
   acquiring one or more radiographic images corresponding to one or more turbine engine blades;
   identifying one or more regions of interest in the one or more radiographic images;
   extracting one or more geometric features of the turbine engine blade located in the one or more regions of interest; and
   analyzing the one or more geometric features to identify one or more geometric defects present in the one or more geometric features of the turbine engine blades, wherein analyzing the one or more geometric features is not dependent on a set statistical parameters or a reference image.

2. The method of claim 1, wherein identifying the one or more regions of interest comprises generating an edge image corresponding to one or more cooling channels in the turbine engine blades, from the one or more radiographic images.

3. The method of claim 2, wherein the edge image is generated using a laplacian edge detection technique.

4. The method of claim 2, wherein identifying the one or more regions of interest further comprises automatically extracting a trailing edge region corresponding to the turbine engine blade, from the edge image.

5. The method of claim 4, wherein extracting the one or more geometric features of the turbine engine blade located in the one or more regions of interest further comprises segmenting one or more trailing edge holes along the trailing edge region of the turbine blade.

6. The method of claim 5, wherein the one or more geometric features are extracted using a plurality of techniques selected from the group consisting of connected components, centroid computation, outlier elimination, hough transforms, second derivative profiles and anisotropic diffusion.

7. The method of claim 5, further comprising applying at least one of a turbine engine blade acceptance criterion and a turbine engine blade rejection criterion based on the one or more extracted geometric features, to identify the one or more geometric defects in the turbine engine blades.

8. The method of claim 7, further comprising classifying one or more of the geometric defects in the turbine blade based on the extracted geometric features and at least one of the turbine engine blade acceptance criterion and the turbine engine blade rejection criteria.

9. The method of claim 8, wherein the one or more geometric defects comprise least one of missing holes, dwells, overdrills, merges, misdrills and scarfs in the cooling holes of the turbine blades.

10. The method of claim 9, wherein at least one of the scarfs and dwells are identified using relative contrast measures.

11. The method of claim 1, wherein the radiographic images are acquired using an X-ray imaging system.

12. A system for automatically identifying geometric defects in turbine engine blades comprising:
a feature segmentation component configured to identify one or more regions of interest in one or more radiographic images corresponding to one or more turbine engine blades;
a feature identification component configured to extract one or more geometric features of the turbine engine blade located in the one or more regions of interest; and
a defect identification component configured to analyze the one or more geometric features to identify one or more geometric defects present in the one or more geometric features of the turbine engine blades, wherein said analysis is not dependent on statistical parameters or reference image.

13. The system of claim 12, wherein the one or more radiographic images are acquired using an X-ray imaging system.

14. The system of claim 12, wherein the feature segmentation component is configured to generate an edge image corresponding to one or more cooling channels in the turbine engine blades, from the one or more radiographic images.

15. The system of claim 14, wherein the feature segmentation component is further configured to automatically extract a trailing edge region corresponding to the turbine engine blade, from the edge image.

16. The system of claim 15, wherein the feature identification component is further configured to segment one or more trailing edge holes along the trailing edge region of the turbine blade.

17. The system of claim 12, wherein the feature identification component is configured to extract the one or more geometric features using a plurality of techniques selected from the group consisting of connected components, centroid computation, outlier elimination, hough transforms, second derivative profiles and anisotropic diffusion.

18. The system of claim 16, wherein the defect identification component is configured to apply at least one of a turbine engine blade acceptance criterion and a turbine engine blade rejection criterion based on the one or more extracted geometric features, to identify the one or more geometric defects in the turbine engine blades.

19. The system of claim 18, wherein the defect identification component is configured to classify the one or more geometric defects in the turbine blade based on the extracted geometric features and at least one of the turbine engine blade acceptance criterion and the turbine engine blade rejection criteria.

20. The system of claim 19, wherein the one or more geometric defects comprise least one of missing holes, dwells, overdrills, merges, misdrills and scarfs in the cooling holes of the turbine blades.

* * * * *